（12） United States Patent
Hatakeyama

(10) Patent No.: US 10,292,613 B2
(45) Date of Patent: May 21, 2019

(54) EYEBLINK DETECTION DEVICE

(71) Applicant: TOYOTA JIDOSHA KABUSHIKI KAISHA, Toyota-shi (JP)

(72) Inventor: Yoshiyuki Hatakeyama, Fuji (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 251 days.

(21) Appl. No.: 15/235,960

(22) Filed: Aug. 12, 2016

(65) Prior Publication Data
US 2017/0055868 A1 Mar. 2, 2017

(30) Foreign Application Priority Data

Aug. 25, 2015 (JP) ................................. 2015-165588

(51) Int. Cl.
*A61B 5/0496* (2006.01)
*A61B 3/113* (2006.01)
(Continued)

(52) U.S. Cl.
CPC .......... *A61B 5/0496* (2013.01); *A61B 3/0025* (2013.01); *A61B 3/0041* (2013.01);
(Continued)

(58) Field of Classification Search
CPC ... A61B 5/0496; A61B 3/0025; A61B 3/0041; A61B 3/113; A61B 5/1103; A61B 5/7282
(Continued)

(56) References Cited

U.S. PATENT DOCUMENTS 5,867,587 A * 2/1999 Aboutalib .............. G08B 21/06
340/576
2014/0276114 A1* 9/2014 Maeda ................. A61B 5/0082
600/479

(Continued)

FOREIGN PATENT DOCUMENTS

JP 2014124308 A * 7/2014

OTHER PUBLICATIONS

JP 2014124308 A (Machine English Translation) (Year: 2014).*

(Continued)

*Primary Examiner* — Daniel L Cerioni
(74) *Attorney, Agent, or Firm* — Oblon, McClelland, Maier & Neustadt, L.L.P.

(57) ABSTRACT

A device disclosure includes a unit that measures an eye potential; and a unit that sets a threshold coefficient based on a frequency characteristic value of eye potential differential values and sets an upper threshold and a lower threshold based on a number obtained by multiplying a standard deviation of the eye potential differential values by the threshold coefficient, and detects a change in the eye potential differential values as the eyeblink waveform wherein the change occurs in the time-series data on the eye potential differential values either when the eye potential differential value becomes larger than the upper threshold and, after that, changes from the upper threshold to the lower threshold within a predetermined time or when the eye potential differential value becomes smaller than the lower threshold and, after that, changes from the lower threshold to the upper threshold within the predetermined time.

14 Claims, 5 Drawing Sheets

(51) Int. Cl.
*A61B 3/00* (2006.01)
*A61B 5/00* (2006.01)
*A61B 5/11* (2006.01)
*A61B 5/18* (2006.01)

(52) U.S. Cl.
CPC ............ *A61B 3/113* (2013.01); *A61B 5/1103* (2013.01); *A61B 5/7282* (2013.01); *A61B 5/18* (2013.01)

(58) Field of Classification Search
USPC ........................................................ 600/587
See application file for complete search history.

(56) References Cited

U.S. PATENT DOCUMENTS

| | | | |
|---|---|---|---|
| 2016/0029919 A1* | 2/2016 | Hebert | A61B 3/10 600/558 |
| 2018/0125357 A1* | 5/2018 | Suzuki | A61B 3/113 |

OTHER PUBLICATIONS

Hiroaki Yuze et al."A computerized identification and data analysis of eyelink EOG waves", Japan Ergonomics Society, vol. 30, No. 5, 7 pages ( with English Abstract).

* cited by examiner

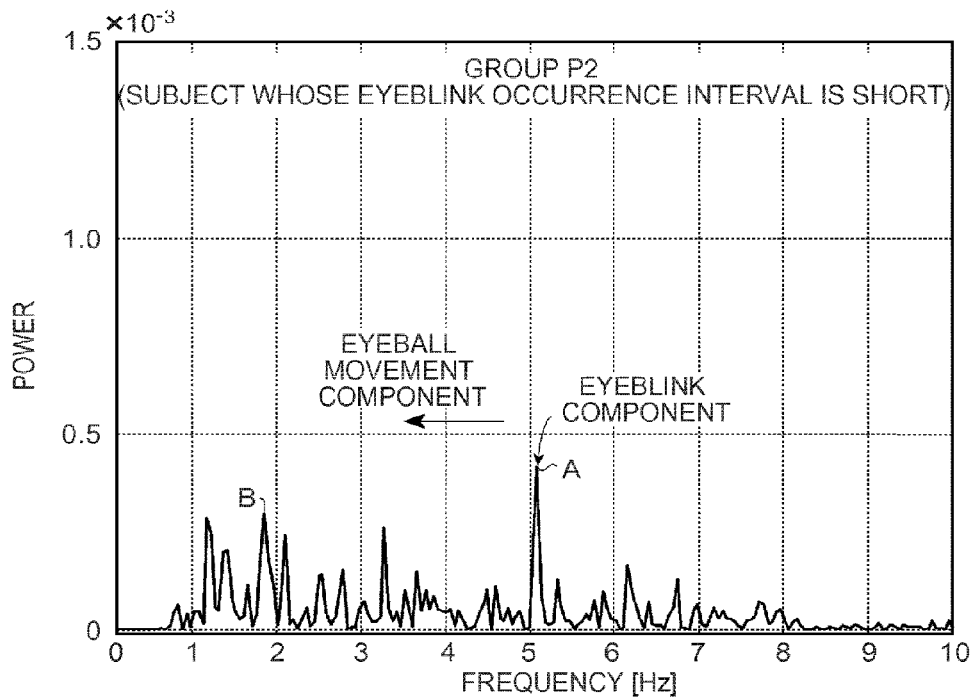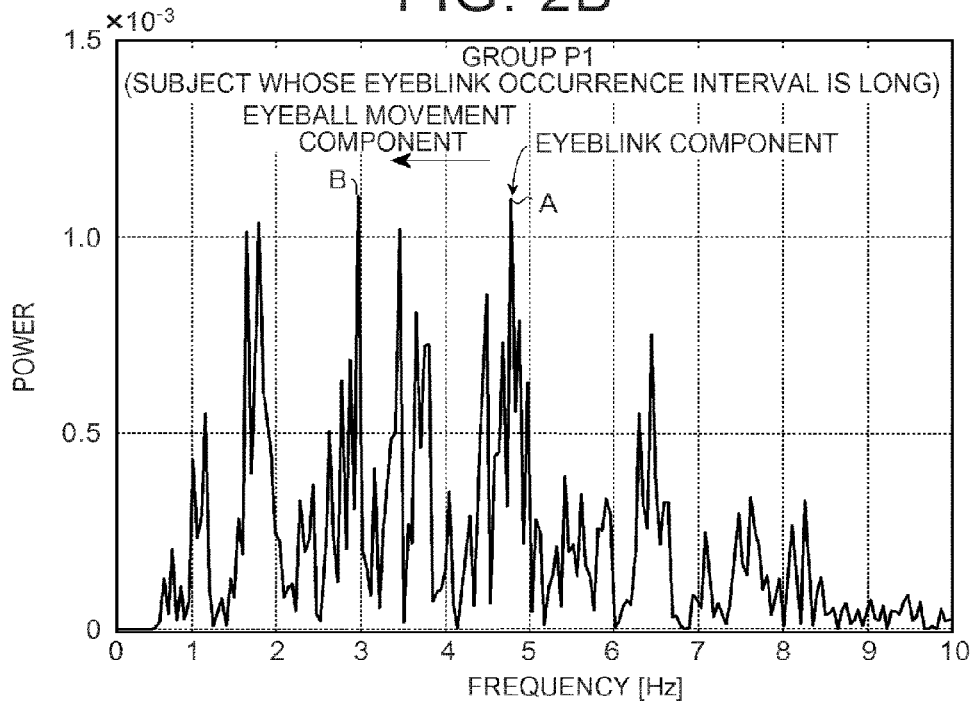

US 10,292,613 B2

EYEBLINK DETECTION DEVICE

INCORPORATION BY REFERENCE

The disclosure of Japanese Patent Application No. 2015-165588 filed on Aug. 25, 2015 including the specification, drawings and abstract is incorporated herein by reference in its entirety.

BACKGROUND

1. Technical Field

The present disclosure relates to a device that detects a human eyeblink (blinking), and more particularly to a device that detects an eyeblink in the waveform of a human electrooculogram (EOG).

2. Description of Related Art

A technology for detecting a human eyeblink is proposed for the purpose of detecting the drowsiness of a human because the frequency of, and a change in, human eyeblinks are associated with the level of the drowsiness of a human. One of the known methods for detecting a human eyeblink include a method that captures the eyelids of a human and detects the opening or closing of the eyelids in the captured image. Another known method is an electrooculogram (EOG) method that, with the electrodes attached around the eyes, detects the potential difference (eye potential) between the cornea and the retina as the eyelids are opened or closed. The outline of the EOG method is as follows. When the eyelids are opened or closed, a temporary eye potential change occurs as schematically shown in FIG. 6A. The EOG method detects such an eye potential change in the eye potential data, measured on a time-series basis, for detecting an eyeblink. In regard to this point, "A computerized identification and data analysis of eyeblink EOG waves" by Hiroaki YUZE & Hideoki TADA, Japan Ergonomics Society Vol. 30, No. 5, pp. 331-337, proposes an algorithm for automatically detecting an eye potential change that is caused when an eyeblink occurs. This algorithm calculates the differential values of eye potential time-series data and then, as an eyeblink, detects a part of the waveform where the differential value exceeds the positive side threshold and the negative side threshold in a row in the waveform of the eye potential differential values within a predetermined time (about 0.2 seconds) as shown in FIG. 6B.

In the differential values of eye potential time-series data in the EOG method described above, the amplitude of the eyeblink waveform varies according to each subject. Therefore, according to the method described in "A computerized identification and data analysis of eyeblink EOG waves" by Hiroaki YUZE & Hideoki TADA, Japan Ergonomics Society Vol. 30, No. 5, pp. 331-337, the negative side threshold and the positive side threshold, used for detecting an eyeblink waveform, are set for each subject as follows, using the average value and the standard deviation of the differential values of the eye potential time-series data of each subject. That is, the negative side threshold is set to the "average value of differential values−2×standard deviation", and the positive side threshold to the "average value of differential values+1×standard deviation". This means that the thresholds are changed according to a difference in the amplitude of eyeblink waveforms. In regard to this point, a study by the inventor of the present disclosure reveals that, when the thresholds are set uniformly based on a constant times the standard deviation of the eye potential differential values of each subject (more exactly, though the difference of the threshold from the average value of the differential values is set to a constant times the standard deviation, the threshold is set virtually to a constant times the standard deviation because the average value of the differential values is approximately 0), it sometimes becomes difficult to accurately detect the eyeblink waveform depending upon some subjects. One of the reasons is that the eyeblink occurrence interval, that is, the occurrence frequency per unit time, differs from subject to subject and, therefore, the ratio of the standard deviation of the differential values of eye potential time-series data to the amplitude of the eyeblink waveform differs from subject to subject. Another reason is that, as described in "A computerized identification and data analysis of eyeblink EOG waves" by Hiroaki YUZE & Hideoki TADA, Japan Ergonomics Society Vol. 30, No. 5, pp. 331-337, the eye potential time-series data includes not only a potential change caused by an eyeblink (eyeblink waveform) but also a potential change caused by a factor other than an eyeblink such as an eyeball movement, with the result that a potential change in the data, caused by a factor other than an eyeblink, is sometimes detected erroneously as an eyeblink waveform.

A further study by the inventor of the present disclosure reveals that using the thresholds, which are set considering the frequency characteristic of the differential values of eye potential time-series data, makes it possible to detect an eyeblink waveform more accurately than before, with fewer detection errors and fewer detection omissions as compared to those before. This knowledge is used in the present disclosure.

SUMMARY

The present disclosure provides a device that detects an eyeblink in the waveform of an electrooculogram and that detects an eyeblink waveform more accurately than before.

An eyeblink detection device according to a first aspect of the present disclosure includes an eye potential measurement unit configured to measure an eye potential of a subject; an eye potential differential value data generation unit configured to generate time-series data on differential values of the eye potential; a frequency characteristic value determination unit configured to determine a frequency characteristic value from the time-series data on the eye potential differential values, the frequency characteristic value representing a frequency characteristic of the eye potential differential values; a threshold setting unit configured to set a threshold coefficient based on the frequency characteristic value of the eye potential differential values and to set an upper threshold and a lower threshold based on a number obtained by multiplying a standard deviation of the differential values in the time-series data on the eye potential differential values by the threshold coefficient, the upper threshold and the lower threshold being used for detecting an eyeblink waveform in the time-series data on the eye potential differential values; an eyeblink waveform detection unit configured to detect a change in the eye potential differential values as the eyeblink waveform, the change occurring in the time-series data either when the eye potential differential value becomes larger than the upper threshold and, after that, changes from the upper threshold to the lower threshold within a predetermined time or when the eye potential differential value becomes smaller than the lower threshold and, after that, changes from the lower threshold to the upper threshold within the predetermined time; and a display unit that outputs an eyeblink detection result based on the eyeblink waveform.

An eyeblink detection device according to a second aspect of the present disclosure includes an eye potential measurement unit that measures an eye potential of a subject; and a signal processing device that generates time-series data on differential values of the eye potential, determines a frequency characteristic value from the time-series data, the frequency characteristic value representing a frequency characteristic of the eye potential differential values, sets a threshold coefficient based on the frequency characteristic value, sets an upper threshold and a lower threshold based on a number obtained by multiplying a standard deviation of the differential values by the threshold coefficient, detects a change in the differential values as an eyeblink waveform, the change occurring in the time-series data either when the differential value becomes larger than the upper threshold and, after that, changes from the upper threshold to the lower threshold within a predetermined time or when the differential value becomes smaller than the lower threshold and, after that, changes from the lower threshold to the upper threshold within the predetermined time, and outputs an eyeblink detection result based on the eyeblink waveform to a display unit.

In the above configuration, the "eye potential measurement unit" may be a unit that measures the potential difference between at least one pair of electrodes attached around an eye so that the potential difference between the cornea and the retina, which is generated as the eyelids are opened or closed, can be measured in an arbitrary mode. Typically, the signal representing the potential difference (eye potential) between the electrodes is A/D converted for use in the subsequent processing. The "time-series data on eye potential differential values" may be a sequence of time-series differential value data obtained by differentiating, in an arbitrary mode, the values of time-series measurement data on the above-described eye potential with respect to time. Preferably, the "time-series data on eye potential differential values" may be the data obtained by differentiating with respect to time the data that is generated by extracting data in a predetermined band, including the frequency band of the eyeblink waveform, from the time-series measurement data on the eye potential via a bandpass filter (or the data that is generated by removing the data in a frequency band higher than and lower than the predetermined band from the time-series measurement data). The "eyeblink waveform" is a waveform corresponding to a potential change caused by an eyeblink. Typically, the "eyeblink waveform" is a waveform that has the shape of a profile drawn in such a way that the data value changes from the value of approximately 0 into one of the positive and negative directions and, after that, changes into the opposite direction again to the value of zero in a relatively short time (typically, 0.1 seconds to 0.4 seconds) (The direction into which the eye potential changes when an eyeblink occurs is determined by the arrangement of the electrodes). The "upper threshold" and the "lower threshold" are the positive side threshold and the negative side threshold respectively for the time-series data on the eye potential differential values. The "predetermined time" is set to a time width corresponding to a period of time during which the eye potential differential value becomes larger than the upper threshold and, after that, changes from the upper threshold to the lower threshold or during which the eye potential differential value becomes smaller than the lower threshold and, after that, changes from the lower threshold to the upper threshold in a usual "eyeblink waveform" (The specific time width may be set on a trial basis). The "frequency characteristic value" is a value representing the frequency characteristic of time-series data on the eye potential differential values. In particular, as will be described in detail later, the value used as the "frequency characteristic value" is a value representing the relation or the ratio between the power of the component (eyeblink waveform component) in the band of the frequency of an eyeblink waveform and the power of the components in a band with a frequency other than that of the eyeblink waveform, for example, the components (non-eyeblink waveform components) of a potential change caused by an eyeball movement. In this specification, the "eyeblink waveform component" and the "non-eyeblink waveform components" refer to components in the time-series data on the eye potential differential values, and the "threshold", when used alone, refers to both the upper threshold and the lower threshold, unless otherwise stated.

The outline of the device of the present disclosure described above is as follows. As with the eyeblink detection method described in "A computerized identification and data analysis of eyeblink EOG waves" by Hiroaki YUZE & Hideoki TADA, Japan Ergonomics Society Vol. 30, No. 5, pp. 331-337, the device of the present disclosure detects the occurrence of an eyeblink in the time-series data on eye potential differential values as described above by detecting a change in the time-series data as an eyeblink waveform when the differential value becomes larger than the upper threshold and, after that, becomes smaller than the lower threshold (when the eye potential changes into positive side), or when the differential value becomes smaller than the lower threshold and, after that, becomes larger than the upper threshold (when the eye potential changes into negative side), within a predetermined time. If the threshold used for detecting the occurrence of an eyeblink is determined uniformly for all subjects based on a constant times the standard deviation of the eye potential differential values, there are sometimes many erroneous detections or detection omissions of an eyeblink waveform as mentioned above. To address this problem, a study by the inventor of the present disclosure reveals that using a threshold, which is set based on a number calculated by multiplying the standard deviation of the differential values by a threshold coefficient that is set for each subject based on the frequency characteristic value of the eye potential differential values ([threshold coefficient]×[standard deviation of differential values]), reduces erroneous detections and detection omissions of an eyeblink waveform, enabling a eyeblink waveform to be detected more accurately. Therefore, in the present disclosure, each of the upper threshold and the lower threshold for detecting an eyeblink waveform is set based on a number calculated by multiplying the standard deviation of the differential values in the time-series data on the eye potential differential values by a threshold coefficient that is set based on the frequency characteristic value of the eye potential differential values. Setting the upper threshold and the lower threshold in this manner increases the accuracy of eyeblink waveform detection. Typically, the upper threshold and the lower threshold are given in the form "average value of eye potential differential values±standard deviation×threshold coefficient". The average value and the standard deviation of the eye potential differential values may be the average value and the standard deviation of the time-series data on the eye potential differential values over an arbitrary period of time. The threshold coefficient may be a value different between the upper threshold and the lower threshold. Because the average value of the differential values is approximately 0 in the form given above, the upper threshold and the lower threshold may be given in the form "±standard deviation× threshold coefficient".

In the configuration described above, the frequency characteristic value may be a value representing the ratio of the power of the non-eyeblink waveform components to the power of the eyeblink waveform component (integral or sum of signal intensities) in the time-series data on the eye potential differential values. In that case, the threshold setting unit may set a threshold coefficient larger when the frequency characteristic value is large than when the frequency characteristic value is small.

(It should be understood that, when the frequency characteristic value is a value representing the ratio of the power of the eyeblink waveform component to the power of the non-eyeblink waveform components in the time-series data on the eye potential differential values, the magnitude of the threshold coefficient when the frequency characteristic value is large is set smaller than when the frequency characteristic value is small)

As will be described in detail in Detailed Description of Embodiment, a study by the inventor of the present disclosure indicates that, in this configuration, an eyeblink waveform component usually occurs in a narrow band around a frequency of approximately 5 Hz (the actual band differs slightly among subjects) in the frequency characteristic of time-series data on the eye potential differential values and that non-eyeblink waveform components, generated by an eyeball movement and so on, tend to have an amplitude relatively smaller than that of an eyeblink waveform component and occur in a relatively wide band (mainly, on the lower frequency side of eyeblink waveform component). In addition, comparison of the frequency characteristic between a subject whose eyeblink occurrence interval is long and a subject whose eyeblink occurrence interval is short indicates that the ratio of the power of the non-eyeblink waveform components to the power of the eyeblink waveform component is relatively high for a subject whose eyeblink occurrence interval is long, that is, non-eyeblink waveform components occur relatively more frequently in the time-series data on the eye potential differential values. Because the dispersion of values in the time-series data is smaller as the occurrence frequency of eyeblinks per unit time is smaller, the standard deviation of the differential values when the eyeblink occurrence interval is long becomes smaller than when the eyeblink occurrence interval is short. Therefore, the ratio of the magnitude of the standard deviation of the differential values to the amplitude of the eyeblink waveform component becomes relatively small.

Considering the points described above, there is a tendency that the occurrence frequency of non-eyeblink waveform components is high and the standard deviation of the differential values is small for a subject whose eyeblink occurrence interval is long. Therefore, to detect an eyeblink waveform component selectively and more reliably, it is preferable that, when setting a threshold, the magnitude of the threshold for the standard deviation of the differential values be set relatively larger for a subject whose eyeblink occurrence interval is long than for a subject whose eyeblink occurrence interval is short in order to prevent a non-eyeblink waveform component from being erroneously detected. In addition, because there is a tendency that the occurrence frequency of non-eyeblink waveform components is relatively higher for a subject whose eyeblink occurrence interval is long as described above, the frequency characteristic value, when used as a value representing the ratio of the power of the non-eyeblink waveform components to the power of the eyeblink waveform component, becomes larger when the eyeblink occurrence interval is long than when the eyeblink occurrence interval is short. This makes it possible to use the frequency characteristic value to determine the length of the eyeblink occurrence interval. Therefore, according to the present disclosure, the threshold coefficient, which is multiplied by the standard deviation of the differential values for setting the threshold, is preferably set larger when the frequency characteristic value is large (when the eyeblink occurrence interval is long) than when the frequency characteristic value is short (when the eyeblink occurrence interval is short).

In one aspect of the embodiments of the present disclosure described above, the frequency characteristic value determination unit may include a unit that calculates the frequency spectrum of the time-series data on the eye potential differential values. In that case, the frequency characteristic value may be a value representing the ratio of the power of non-eyeblink waveform components to the power of eyeblink waveform component in the frequency spectrum of the eye potential differential values. In this case, in one specific aspect, the frequency characteristic value may be the ratio of the maximum value of the power of the non-eyeblink waveform components to the power of the eyeblink waveform component. As described above, the magnitude of the threshold coefficient may be set larger when the frequency characteristic value is large than when the frequency characteristic value is small. The eyeblink waveform component is selected easily because it is detected usually as one peak in the frequency band of the eyeblink waveform component in the frequency spectrum of the eye potential differential values. On the other hand, for the non-eyeblink waveform components, several peaks of power occur in a relatively wide band in the frequency spectrum of the eye potential differential values and, therefore, the maximum value of the peaks may be selected. In addition, in another aspect of the value that is used as the frequency characteristic value and that represents the ratio of the power of the non-eyeblink waveform components to the power of the eyeblink waveform component in the frequency spectrum of the eye potential differential values, the frequency characteristic value may be the sum of the powers in the frequency spectrum. In this case too, the magnitude of the threshold coefficient when the frequency characteristic value is large may be set larger than when the frequency characteristic value is small as described above. As already mentioned before, the eyeblink waveform component usually occurs as one peak in the frequency spectrum of the eye potential differential values, while the non-eyeblink waveform components occur in a relatively wide band. In addition, because the sum of the powers in the frequency spectrum increases as the number of non-eyeblink waveform components increases, the sum of the powers in the frequency spectrum may be used as an index representing the ratio of the power of the non-eyeblink waveform components to the power of the eyeblink waveform component in the frequency spectrum of the eye potential differential values.

In setting the threshold coefficients described above, the threshold coefficients may be set corresponding to the frequency characteristic value. The specific numeric values may be determined in advance by experiment. In addition, to perform eyeblink detection for the subjects, the subjects may be classified based on the frequency characteristic value and the threshold coefficients may be set for each of the groups of the subjects. In this case, the subjects are classified into a plurality of groups according to their frequency characteristic values, and the threshold coefficients provided for each group are used to perform eyeblink detection.

In setting the thresholds, the standard deviation of the differential values in the time-series data on the eye potential differential values for a subject is required. In that case, because the frequency of eyeblinks per unit time for a subject whose eyeblink occurrence interval is long is low, it is preferable that the standard deviation be calculated using time-series data with a time width longer than that of the short eyeblink occurrence interval in order to increase the accuracy of the standard deviation. In regard to this point, a study by the inventor of the present disclosure indicates that the frequency characteristic value may be used as an index of the length of the eyeblink occurrence interval as described above. Therefore, in the configuration of the present disclosure described above, the interval width of the time-series data for calculating the standard deviation of the differential values in the time-series data on the eye potential differential values may be set based on the frequency characteristic value. This makes it possible to use the differential values of the time-series data with an interval width, which is set corresponding to the length of the eyeblink occurrence interval, for calculating the standard deviation more accurately. When the frequency characteristic value is used as a value representing the ratio of the power of the non-eyeblink waveform components to the power of the eyeblink waveform component in the time-series data on the eye potential differential values, the interval width of the time-series data when the frequency characteristic value is large may be set larger than when the frequency characteristic value is small.

In the embodiment, if an eyeblink waveform in the time-series data on the eye potential differential values is detected, the eyeblink time can be detected from its length. Therefore, an eyeblink time detection unit, which detects the eyeblink time in the detected eyeblink waveform, may be provided.

Thus, when detecting an eyeblink waveform in the time-series data on the eye potential differential values using the thresholds, the configuration of the present disclosure described above, in which the thresholds are set appropriately for each subject, allows an eyeblink waveform to be detected more accurately than before. This leads to a reduction in the detection omission of eyeblink waveform components and in the erroneous detection of non-eyeblink waveform components as eyeblink waveform components. In addition, eyeblink detection via electrooculogram requires a smaller calculation amount and a lower cost than eyeblink detection via video camera images. This means that, as the accuracy of eyeblink detection via electrooculogram increases, electrooculogram will be used more advantageously in eyeblink detection, for example, for drowsiness detection.

The other purposes and advantages of the present disclosure will be easily understood from the description of the preferred embodiments of the present disclosure given below.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 1C is a diagram showing the principle of eyeblink waveform detection.

FIG. 2A is a diagram showing an example of the frequency spectrum of time-series data on the eye potential differential values of a subject whose eyeblink occurrence interval is short, and FIG. 2B is a diagram showing an example of the frequency spectrum of time-series data on the eye potential differential values of a subject whose eyeblink occurrence interval is long;

DETAILED DESCRIPTION OF EMBODIMENTS

Figure 1A:
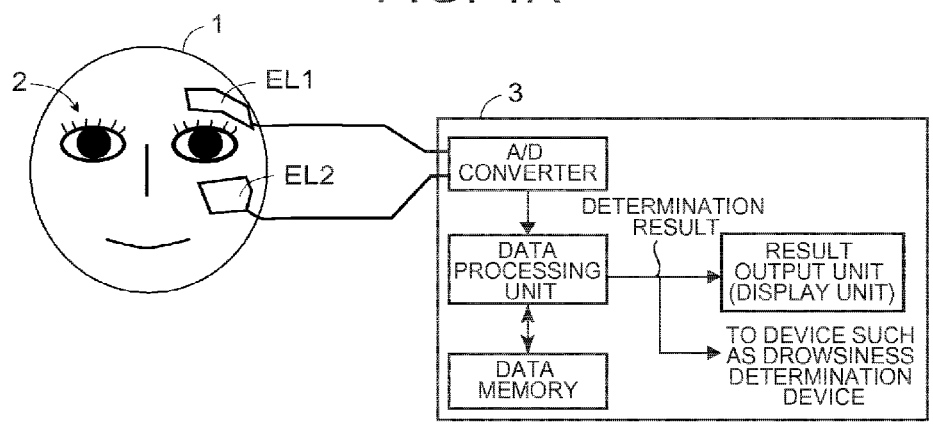
FIG. 1A is a diagram schematically showing the configuration of an eyeblink detection device of the present disclosure.

Preferred embodiments of the present disclosure are described in detail below with reference to the drawings. In the figures, the same reference numeral is used for the same component.

Device Configuration

As with the system described in "A computerized identification and data analysis of eyeblink EOG waves" by Hiroaki YUZE & Hideoki TADA, Japan Ergonomics Society Vol. 30, No. 5, pp. 331-337, an eyeblink detection device of the present disclosure measures the eye potential of a subject by means of the EOG method. The device checks the time-series data on the eye potential differential values for detecting an eyeblink waveform, generated by the occurrence of an eyeblink, to detect that an eyeblink has occurred. Referring to FIG. 1A, the basic configuration of the eyeblink detection device of the present disclosure is described. First, at least one pair of electrodes EL1 and EL2 is attached around an eye and an eyelid 2 of a face 1 of a subject, and the potential difference between the electrodes is serially sent to a signal processing device 3 as the eye potential signal. In the signal processing device 3, an A/D converter serially digitizes the eye potential signal, and a data processing unit uses the digitized eye potential signal, or the time-series data on the measured values of the eye potential, to perform various types of processing for detecting an eyeblink that will be described later. The data processing unit is configured to communicate with a data memory and store, as necessary, the time-series data on the eye potential measured values, their differential value data, and other arithmetic processing results in the data memory. The data processing unit is also configured to read various numeric values, stored in the data memory, for use in the arithmetic processing. The arithmetic processing results produced by the data processing unit may be sent, as necessary, to a result output unit, such as a display, for display thereon. In addition, the eyeblink detection result may be sent to any device for drowsiness determination. Typically, the signal processing device 3 is a computer. In the normal mode, the computer includes a CPU, a storage device, and input/output devices (I/O) that are interconnected by a bidirectional common bus not shown. The operation of the units of the eyeblink detection device is implemented by the programs executed by the CPU.

Principle of Eyeblink Detection

Figure 1B:
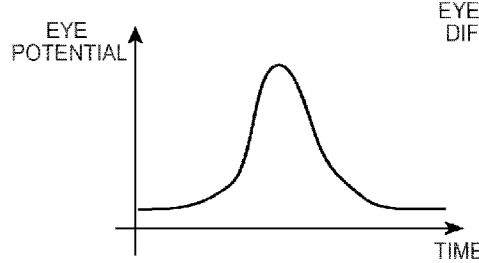
FIGS. 1B and 1C are diagrams schematically showing a change in the eye potential during an eyeblink obtained by the EOG method and its differential values respectively.
Figure 1C:
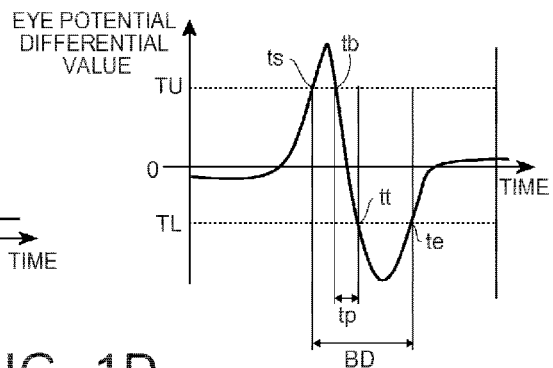
Figure 6A:
FIGS. 6A and 6B are diagrams schematically showing a change in an eye potential during an eyeblink obtained by the conventional EOG method in the prior art and the differential values respectively. The eye potential change direction is the reverse of that shown in FIG. 1B because the arrangement of the anode and the cathode is the reverse of that in FIG. 1B.
Figure 6B:
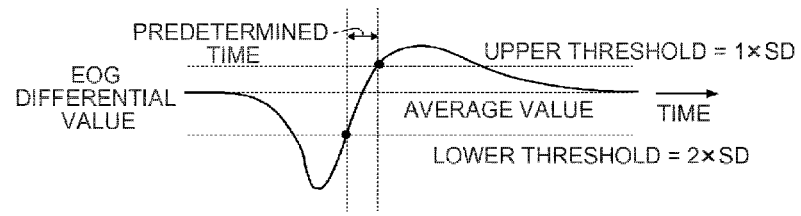

In detecting an eyeblink, the device according to the present disclosure serially measures the eye potential of a subject and, when an eyeblink occurs, detects the potential change, such as the one schematically shown in FIG. 1B, to detect the eyeblink as described above. However, because the actual eye-potential serial measurement data (time-series data) includes not only data on a potential change caused by an eyeblink but also data on a potential change caused by other factors such as an eyeball movement, it is necessary to identify the characteristic of the waveform of a potential change, caused by an eyeblink, to selectively detect an eyeblink. To do so, the eyeblink detection technology according to the present disclosure calculates the time differential values of the eye potential measurement data to generate time-series data on the eye potential differential values. Then, based on the time-series data on the eye potential differential values, the technology detects the differential value waveform (eyeblink waveform) corresponding to the potential change caused by an eyeblink as shown in FIG. 1C. More specifically, this eyeblink waveform is a waveform that has the shape of a profile drawn in such a way that the data value (differential value) changes from the value of approximately 0 into the positive direction and, after a relatively short period of time, changes into the negative direction, and then changes into the positive direction again to the value of zero, as shown in the figure. The amplitude of the waveform is usually larger than the amplitude of the waveform (non-eyeblink waveform) of a potential change such as that of eyeball movement. Therefore, in detecting an eyeblink waveform, the upper threshold TU and the lower threshold TL are set on the positive side and the negative side respectively and, if the differential value exceeds the upper threshold TU and then, within a predetermined time tp, changes from the upper threshold TU (point tb) to the lower threshold TL (point tt), the waveform is identified as an eyeblink waveform (it is assumed that the value of a non-eyeblink waveform reaches neither the upper threshold TU nor the lower threshold TL). The predetermined time tp, which may be set in advance on a trial basis, is set typically, for example, to 0.2 seconds. The upper threshold TU and the lower threshold TL, which should be set according to the amplitude of the eyeblink waveform, differ according to each subject. Therefore, for example, in the system described in "A computerized identification and data analysis of eyeblink EOG waves" by Hiroaki YUZE & Hideoki TADA, Japan Ergonomics Society Vol. 30, No. 5, pp. 331-337, the upper threshold and the lower threshold are set as follows using the average value and the standard deviation of the eye potential differential values in the time-series data in an arbitrary time interval: upper threshold=average value+2×standard deviation . . . (1a) and lower threshold=average value−1×standard deviation . . . (1b). It may be said that, because the average value of the differential values is approximately 0, each threshold is set uniformly to a constant times the standard deviation for any subject. (The direction of the potential change during an eyeblink is determined by the arrangement of the electrodes attached to the face of a subject. The direction of a potential change caused by an eyeblink exemplified in FIG. 6, which is described in "A computerized identification and data analysis of eyeblink EOG waves" by Hiroaki YUZE & Hideoki TADA, Japan Ergonomics Society Vol. 30, No. 5, pp. 331-337, is the negative direction that is the reverse of the direction in this embodiment. This is because the arrangement of the anode and the cathode is the reverse of the arrangement in this embodiment. The expressions (1a) and (1b) given above indicate the thresholds that are used when the direction of the potential change caused by an eyeblink is the positive direction).

Figure 1D:
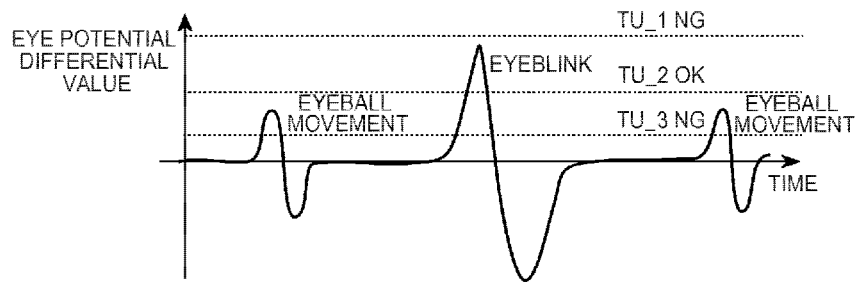
FIG. 1D is a diagram schematically showing time-series data on the eye potential differential values that includes wave components other than those of an eyeblink (components caused by an eyeball movement)

However, as mentioned in Summary, when each of the thresholds is set to a constant times the standard deviation as described above, there is sometimes a case in which the waveform of a potential change caused by an eyeball movement (non-eyeblink waveform) is detected erroneously as an eyeblink waveform (erroneous detection of an eyeblink waveform), or the detection omission of an eyeblink waveform occurs more frequently, depending upon the subject. More specifically, to detect an eyeblink waveform selectively and more reliably, the magnitude of the threshold (for example, upper threshold) must be set to a value (TU_2) larger than the amplitude of a non-eyeblink waveform such as that of an eyeball movement and smaller than the amplitude of the eyeblink waveform as schematically shown in FIG. 1D. However, when the threshold is set approximately to a constant times the standard deviation, the magnitude of the threshold is sometimes set to a value (TU_3) that is smaller than the amplitude of a non-eyeblink waveform depending upon the subject. In addition, when the constant multiplied by the standard deviation is increased to avoid this condition, the value sometimes becomes a value (TU_1) that is larger than the amplitude of the eyeblink waveform.

In regard to this point, a study by the inventor of the present disclosure reveals that the threshold is not appropriately is set because of the following two reasons: (1) The standard deviation of the eye potential differential values varies according to the length of an eyeblink occurrence interval. (2) There is a difference in the occurrence frequency of a non-eyeblink waveform between a subject whose eyeblink occurrence interval is long and a subject whose eyeblink occurrence interval is short.

The following describes the reasons more in detail. First, when calculating the standard deviation of the differential values from the time-series data on the eye potential differential values, a comparison between the standard deviation for a long eyeblink occurrence interval and the standard deviation for a short eyeblink occurrence interval indicates that a variation in the time-series data values of the former is smaller. This means that the standard deviation, which is an index representing a variation in the values, becomes relatively smaller and, therefore, the magnitude of the threshold, which is virtually set to a constant times the standard deviation, becomes smaller. On the other hand, because the amplitude of an eyeblink waveform does not change greatly according to the length of the eyeblink occurrence interval, the magnitude of the threshold becomes relatively smaller in relation to the amplitude of the eyeblink waveform when the eyeblink occurrence interval is long.

In addition, an examination of the time-series data on the eye potential differential values both for a subject whose eyeblink occurrence interval is long and for a subject whose eyeblink occurrence interval is short indicates that the occurrence frequency of a non-eyeblink waveform of the subject whose eyeblink occurrence interval is long is high. That is, for a subject whose eyeblink occurrence interval is long, there is a tendency that the potential change in the eyeball movement and so on occurs more frequently. The frequency spectrum diagrams in FIGS. 2A and 2B show the actual calculation result of the frequency spectrum of time-series data on the eye potential differential values for several subjects. As shown in FIGS. 2A and 2B, in the frequency spectrum, a peak corresponding to the eyeblink waveform component occurs around 5 Hz while the non-eyeblink waveform components such as those of an eyeball movement occur in a wide range in a frequency band lower than that of the eyeblink waveform component. A comparison of the frequency spectrum between a subject whose eyeblink occurrence interval is long (FIG. 2B) and a subject whose eyeblink occurrence interval is short (FIG. 2A) indicates that the ratio of the power of the non-eyeblink waveform components to the power of the eyeblink waveform component is relatively high for the subject whose eyeblink occurrence interval is long. That is, it is understood that the occurrence frequency of the non-eyeblink waveform components is high for the subject whose eyeblink occurrence interval is long. In addition, for a subject whose eyeblink occurrence interval is long, the magnitude of the threshold in relation to the amplitude of the eyeblink waveform is small as described above. This further increases the rate at which a non-eyeblink waveform component is detected erroneously as an eyeblink waveform component.

Therefore, in setting a threshold, the above knowledge should be taken into consideration. As described above, for a subject whose eyeblink occurrence interval is long, the calculated standard deviation is small and the occurrence frequency of non-eyeblink waveform components is high. Therefore, when setting a threshold for detecting an eyeblink waveform component for a subject whose eyeblink occurrence interval is long, the conclusion is that (1) the standard deviation should be set larger to compensate for a relatively small standard deviation and (2) the ratio of the magnitude of the threshold to the standard deviation should be set higher than that of a subject whose eyeblink occurrence interval is short to prevent a non-eyeblink waveform component from being erroneously detected as an eyeblink waveform component.

Thus, in detecting an eyeblink according to the present disclosure, the processing for setting a threshold for detecting an eyeblink waveform described above is improved so that the coefficient multiplied by the standard deviation may be changed according to the length of the eyeblink occurrence interval. In regard to this point, it is already found, as described above, that the length of the eyeblink occurrence interval tends to be associated with the frequency characteristic of time-series data on the eye potential differential values, in particular, with the magnitude of the ratio of the power of non-eyeblink waveform components to the power of an eyeblink waveform component. Therefore, in the embodiment of the present disclosure, the magnitude of the ratio of the power of non-eyeblink waveform components to the power of an eyeblink waveform component is used as an index for the length of the eyeblink occurrence interval.

More specifically, the threshold is set in the following form: upper threshold=average value+standard deviation×upper-threshold coefficient . . . (2a) and lower threshold=average value−standard deviation×lower-threshold coefficient . . . (2b). In setting the thresholds in this manner, the upper-threshold coefficient and the lower-threshold coefficient are set based on the ratio of the power of non-eyeblink waveform components to the power of an eyeblink waveform component so that the coefficients are larger when this ratio is high than when this ratio is low. This configuration allows the ratio of the magnitude of the threshold to the standard deviation to be set higher when the eyeblink occurrence interval of a subject is long than when the eyeblink occurrence interval of a subject is short, thus efficiently avoiding the erroneous detection of a non-eyeblink waveform component as an eyeblink waveform component. This configuration also prevents the ratio of the magnitude of the threshold to the standard deviation from being set meaninglessly high when eyeblink occurrence interval of a subject is short, thus resulting in reducing the detection omissions of an eyeblink waveform component that may occur due to a too large magnitude of the threshold.

The average value and the standard deviation of the eye potential differential values, which are used for calculating the thresholds, are calculated using the values of time-series data with an arbitrary time width. The eyeblink occurrence frequency per unit time is low when the eyeblink occurrence interval is long as described above. Therefore, if the time-series data values with the same time width as that when the eyeblink occurrence interval is short are used for calculating the average value and the standard deviation when the eyeblink occurrence interval is long, the accuracy of the average value and the standard deviation becomes relatively low. To address this problem, it is desirable that the time width of time-series data used for calculating the average value and the standard deviation of the eye potential differential values be also set according to the length of the eyeblink occurrence interval in order to increase the accuracy of the average value and the standard deviation of the eye potential differential values. That is, the time width should also be set based on the ratio of the power of non-eyeblink waveform components to the power of eyeblink waveform component in the frequency characteristic of the time-series data on the eye potential differential values.

Thus, in the embodiment of the present disclosure, the upper-threshold coefficient, the lower threshold coefficient, and the time width of time-series data used for calculating the average and the standard deviation of the eye potential differential values (hereinafter called "threshold-setting time width") are set based on the ratio of the power of non-eyeblink waveform components to the power of eyeblink waveform component in the frequency characteristic of time-series data on the eye potential differential values.

The ratio of the power of non-eyeblink waveform components to the power of eyeblink waveform component in the frequency characteristic of time-series data on eye potential differential values may be determined for each subject by any method using the time-series data on the eye potential differential values over an arbitrary period of time after eyeblink detection is started for the subject. A specific index value, which represents the ratio of the power of non-eyeblink waveform components to the power of eyeblink waveform component, as well as the operation of the device, will be described below.

Device Operation

In the eyeblink detection processing performed by the device of the present disclosure, the potential difference between the electrodes attached to the face of a subject are serially measured. At the same time, the programs are executed to generate time series data on the eye potential differential values using the time-series data on the measured potential differences and to detect an eyeblink waveform using the time-series data on the eye potential differential values.

Figure 3A:
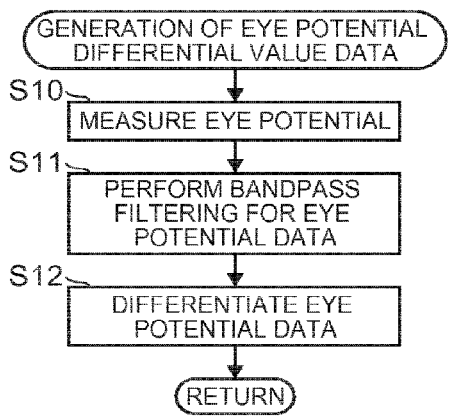
FIG. 3A is a diagram showing, in the form of a flowchart, an example of the generation processing of time-series data on eye potential differential values performed by the device of the present disclosure.
Figure 4A:
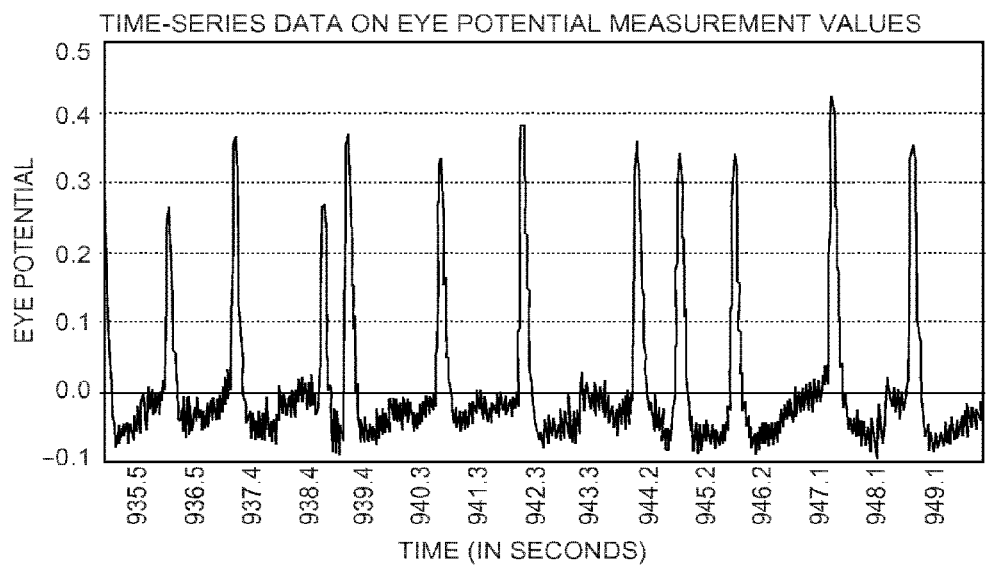
FIG. 4A is a diagram showing an example of time-series data on eye potential measurement values.
Figure 4B:
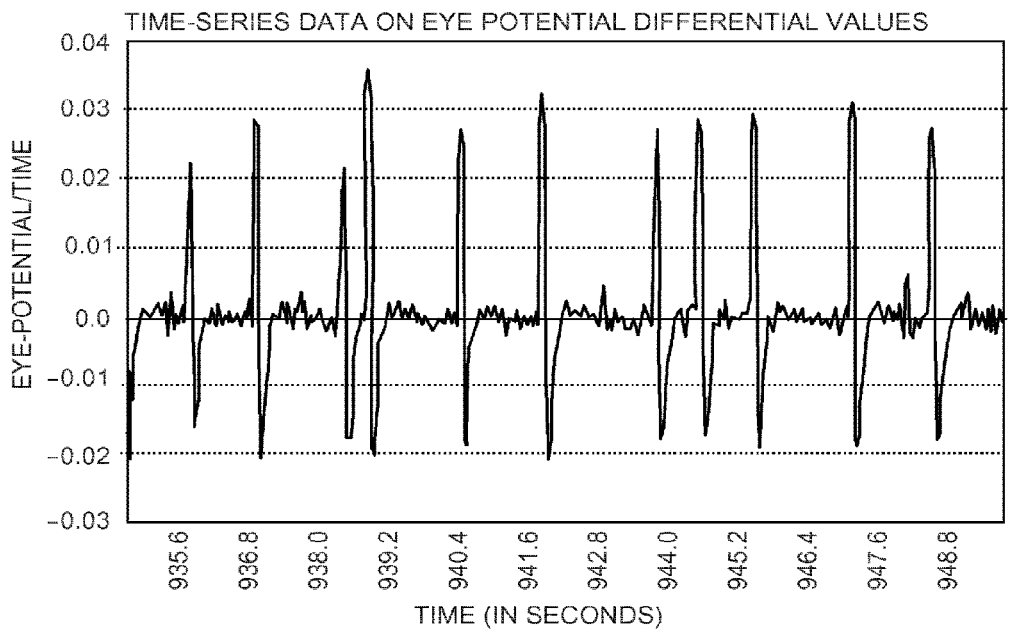
FIG. 4B is a diagram showing an example of time-series data on the eye potential differential values.

(1) Time-Series Data Generation Processing for Eye Potential Differential Values First, referring to FIG. 3A, the time-series data generation processing for eye potential differential values is described. As shown in FIG. 1A, the potential difference between the electrodes attached to the face of a subject is serially digitized by the A/D converter, and the time-series data on the eye-potential measured values is generated as exemplified in FIG. 4A (step S10). The time-series data on the eye potential measured values may be stored in the data memory. The time-series data on the eye potential measured values, which includes not only the potential change caused by an eyeblink but also high-frequency components such as DC components and noises, is filtered by a bandpass filter to remove these components (step S11). For example, a bandpass filter with a low-pass cutoff frequency of 0.7 Hz and a high-pass cutoff frequency of 10 Hz may be used. High-frequency components such as noises may also be removed by the smoothing processing. After that, the time-series data on the eye potential measured values, from which DC components and high-frequency components have been removed, are differentiated with respect to time (step S12) to generate the time-series data on the eye potential differential values such as that exemplified in FIG. 4B. The generated time-series data on the eye potential differential values may be stored in the data memory. The processing, from the A/D conversion of the potential difference between the electrodes to the generation of the time-series data on the eye potential differential values, may be serially performed independently of the eyeblink detection processing that will be described below.

(2) Eyeblink Detection Processing

Figure 3B:
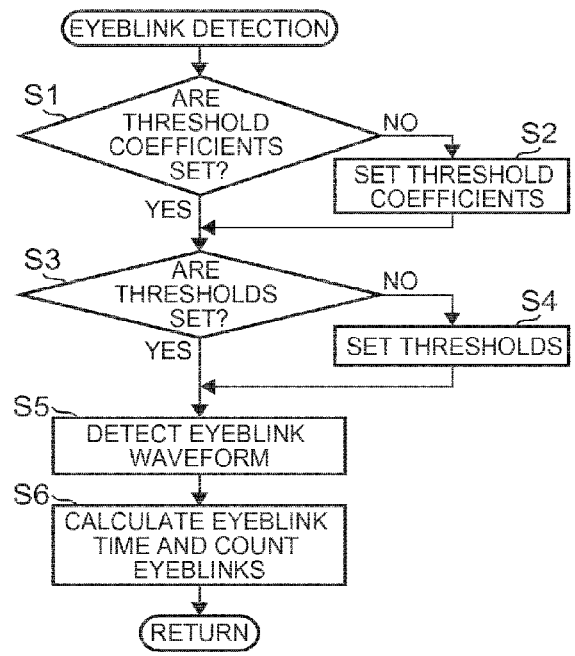
FIG. 3B is a diagram showing, in the form of a flowchart, an example of the eyeblink detection processing performed by the device of the present disclosure.

Next, referring to FIG. 3B, the outline of the eyeblink detection processing is described. A check is made whether the threshold coefficients described above are set (step S1) and whether the thresholds are set (step S3). If the threshold coefficients and/or thresholds are not set, the setting processing (step S2 and/or step S4) is performed respectively and, after the thresholds are set, the eyeblink waveform detection processing is performed for the time-series data on the eye potential differential values (step S5). Each of a sequence of processing is described in detail below.

(a) Threshold Coefficient Setting Processing

Figure 3C:
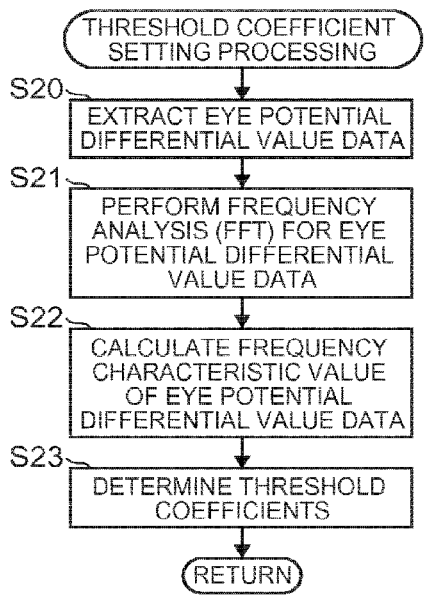
FIG. 3C is a diagram showing, in the form of a flowchart, an example of the threshold coefficient setting processing performed by the device of the present disclosure.

Referring to FIG. 3C, the threshold coefficient setting processing is described. First, the time-series data on the eye potential differential values with an arbitrary time width, stored in the data memory, is extracted (step S20), and the frequency analysis calculation (for example, FFT calculation) is performed for the data (step S21). The time-series data on the eye potential differential values that is extracted is typically data with an arbitrary time width beginning at the start of eyeblink detection, for example, data with the time width of 15 seconds but is not limited to this time width. The frequency analysis calculation, if performed, gives the frequency spectrum of the time-series data on the eye potential differential values as exemplified in FIG. 2A and FIG. 2B. For this frequency spectrum, the frequency characteristic value representing the frequency characteristic, more specifically, the value representing the ratio of the power of non-eyeblink waveform components to the power of an eyeblink waveform component, is calculated (step S22).

In one form of the frequency characteristic value, which represents the ratio of the power of non-eyeblink waveform components to the power of eyeblink waveform component, may be the ratio of the maximum of the power of the non-eyeblink waveform components to the power of the eyeblink waveform component. As understood by referring to FIG. 2A or FIG. 2B, the eyeblink waveform component occurs as one peak around 5 Hz, while the non-eyeblink waveform components caused by an eyeball movement and so on occur in a wide range in the frequency spectrum of the time-series data on the eye potential differential values. Therefore, it is possible to perform arbitrary peak detection processing around 5 Hz for the power of the eyeblink waveform component to obtain the power value A of the detected peak. In addition, it is possible to perform arbitrary peak detection processing for the power of the non-eyeblink waveform components in a band lower than that of the peak of the eyeblink waveform component to obtain the power value B that is the maximum power of the components. In this manner, the frequency characteristic value C is given in this case by the expression C=B/A . . . (3).

Another form of the frequency characteristic value that represents the ratio of the power of the non-eyeblink waveform components to the power of the eyeblink waveform component may be the sum value F of the powers of the frequency spectrum. As described above, the eyeblink waveform component usually occurs as one peak in the frequency spectrum of the eye potential differential values. On the other hand, the non-eyeblink waveform components occur in a relatively wide band and, as the number of non-eyeblink waveform components increases, the sum of the powers of the frequency spectrum increases. Therefore, the sum value F of the powers of the frequency spectrum is used as an index that represents the ratio of the power of the non-eyeblink waveform components to the power of the eyeblink waveform component. A still another form of the frequency characteristic value may be G=Sum value F of the powers of frequency spectrum/Power value A of eyeblink waveform component.

In a typical example, the value of C and the value of F for the length of an eyeblink occurrence period is as follows.

TABLE 1

| Eyeblink occurrence interval (average value) | Value of C | Value of F ($\times 10^{-3}$) |
| --- | --- | --- |
| Shorter than 5 seconds | Smaller than 0.8 | 10 |
| Equal to or longer than 5 seconds and shorter than 30 seconds | 0.8 to 0.9 | 20 |
| Equal to or longer than 30 seconds | 0.9 or larger | 40 |

It is confirmed in the above table that the value of C and the value of F increase as the eyeblink occurrence period is longer.

In the frequency characteristic of the time-series data on eye potential differential values, the band where the eyeblink waveform component occurs and the band where the non-eyeblink waveform components occur are approximately known. Therefore, instead of performing the frequency analysis as described above, the discrimination processing may be performed by means of a bandpass filter to extract the power of the eyeblink waveform component and the power of the non-eyeblink waveform components for calculating the frequency characteristic value.

After the frequency characteristic value C, F, or G is determined as described above, the upper threshold coefficient U, lower threshold coefficient L, and threshold setting time width W are set according to the frequency characteristic value (step S23). The upper threshold coefficient U, lower threshold coefficient L, and threshold setting time width W, which are set by referencing the frequency characteristic value, may be set in one of the modes described below.

In the first mode, a subject is classified into one of the two groups, P1 and P2, according to the magnitude of the frequency characteristic value C (F or G may also be used. The same applies to the description below). The upper threshold coefficient U, lower threshold coefficient L, and threshold setting time width W are set for each group (that is, the value is set in two levels for each of U, L, and W according to the frequency characteristic value). Therefore, if a subject is classified into one of the groups P1 and P2, then U, L, and W, which are set for the group into which the subject is grouped, are used in calculating the thresholds for detecting the eyeblink waveform of the subject. More specifically, the subject is classified into one of P1 and P2 as follows: the subject is classified into P1 (group of long eyeblink occurrence interval) when C≥D, and into P2 (group of short eyeblink occurrence interval) when C<D, where D is a predetermined value that may be set to an appropriate value by experiment. U, L, and W may be set for each of groups P1 and P2 as shown below.

TABLE 2

|  | P1 | P2 |
|---|---|---|
| Upper threshold coefficient U | 6 | 2 |
| Lower threshold coefficient L | 3 | 1 |
| Threshold setting time width W (in seconds) | 180 | 30 |

Therefore, when a subject is classified, for example, into group P1 based on the frequency characteristic value, U, L, and W of group P1 are used for setting the thresholds. It should be understood that U, L, and W of group P1 (long eyeblink occurrence interval) are set larger than those of group P2 (short eyeblink occurrence interval). In addition, it should be understood that the specific values given above are exemplary only and that the actual values are not limited to those values. In practice, these values are set appropriately by experiment according to the measurement conditions. U, L, and W may be set in the same manner as described above when the frequency characteristic value is F or G.

In the second mode, a subject is classified into one of the groups (more groups than those in first mode, for example, Pa, Pb, Pc, Pd, and Pe) according to the magnitude of the frequency characteristic value C. The upper threshold coefficient U, lower threshold coefficient L, and threshold setting time width W are set for each group. More specifically, a subject is classified into one of Pa, Pb, Pc, Pd, and Pe as follows. The subject is classified into Pa (group of longest eyeblink occurrence interval) when C≥D4, into Pb when D4>C≥D3, into Pc when D3>C≥D2, into Pd when D2>C≥D1, and into Pe (group of shortest eyeblink occurrence interval) when D1>C, where D1 to D4 are predetermined values (D4>D3>D2>D1) that may be set to appropriate values by experiment. U, L, and W may be set for each of groups Pa, Pb, Pc, Pd, and Pe as shown below.

TABLE 3

|  | Pa | Pb | Pc | Pd | Pe |
|---|---|---|---|---|---|
| Upper threshold coefficient U | 6 | 5 | 4 | 3 | 2 |
| Lower threshold coefficient L | 3 | 2.5 | 2 | 1.5 | 1 |
| Threshold setting time width W (in seconds) | 180 | 143 | 105 | 68 | 30 |

Therefore, when a subject is classified, for example, into group Pc based on the frequency characteristic value, U, L, and W of group Pc are used for setting the thresholds. It should be understood that U, L, and W are all set such that the longer the eyeblink occurrence interval is, the larger the values are. In addition, it should be understood that the specific values given above are exemplary only and that the actual values are not limited to those values. In practice, these values are set appropriately by experiment according to the measurement conditions. U, L, and W may be set in the same manner as described above when the frequency characteristic value is F or G. It should also be understood that any number of groups may be set.

In the third mode, the upper threshold coefficient U, lower threshold coefficient L, and threshold setting time width W may be set each as a function that monotonically increases with the frequency characteristic value C. More specifically, U, L, and W may be set as follows. $U=k_U C$, $L=k_L C$, and $W=k_W C$, where $k_U$, $k_L$, and $k_W$ are positive numbers that may be set appropriately by experiment.

(b) Threshold Setting Processing

Figure 3D:
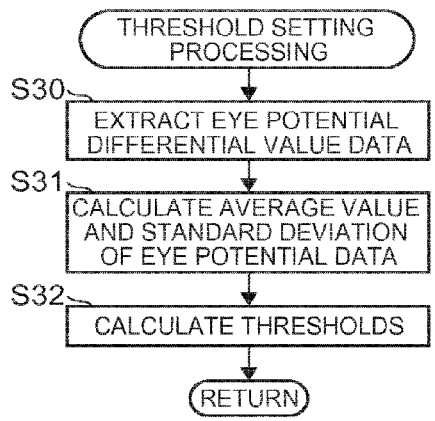
FIG. 3D is a diagram showing, in the form of a flowchart, an example of the threshold setting processing performed by the device of the present disclosure.

Referring to FIG. 3D, the threshold setting processing is described. After the upper threshold coefficient U, lower threshold coefficient L, and threshold setting time width W are set according to the frequency characteristic value as described above, the upper threshold TU and the lower threshold TL are set using those values. In the processing, the time-series data on the eye potential differential values with the threshold setting time width W is extracted from the data memory (step S30), and the average value M and the standard deviation SD of the time-series data are calculated (step S31). Using the upper threshold coefficient U and the lower threshold coefficient L, the upper threshold TU and the lower threshold TL are calculated respectively by TU=M+SD×U . . . (4a) and TL=M−SD×L . . . (4b) (step S32).

(c) Eyeblink Waveform Detection Processing

Referring again to FIG. 3B, after the upper threshold TU and the lower threshold TL are calculated, the eyeblink waveform detection processing is performed for the time-series data on the eye potential differential values (step S5). Referring again to FIG. 1C, the eyeblink waveform detection processing is described in detail. If conditions 1 to 4 given below are satisfied for the time-series data, the corresponding part of an eyeblink waveform is an eyeblink waveform and it is determined that an eyeblink occurs. Condition 1: The differential value becomes larger than the upper threshold TU (ts). Condition 2: After ts, the differential value becomes smaller than the upper threshold TU (tb). Condition 3: After tb, the differential value becomes smaller than the lower threshold TL (tt). Condition 4: The time interval between tb and tt is shorter than the predetermined time tp. The predetermined time tp, which is a value that can be obtained in a usual eyeblink waveform as described above, is set, for example, to 0.2 seconds. As an additional condition, the following condition may be added. Condition 5: After tt, the differential value becomes larger than the lower threshold TL (te). It should be understood that, after the thresholds are set, the eyeblink detection processing described above may be performed almost in real time (at the same time the time-series data on the eye potential differential values is calculated).

Because the time of the point ts and the time of the point te are detected as described above, the eyeblink time BD (length of time from the moment the eyelids are closed to the time the eyelids are opened) may be measured based on te−ts in the present disclosure (step S6). The eyeblink time BD may be used, for example, for drowsiness determination.

Example of Eyeblink Detection

Figure 5A:
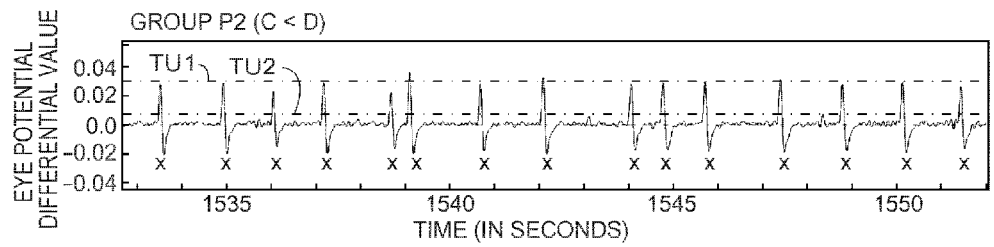
FIG. 5A is a diagram showing an example of time-series data on the eye potential differential values of a subject whose eyeblink occurrence interval is short.
Figure 5B:
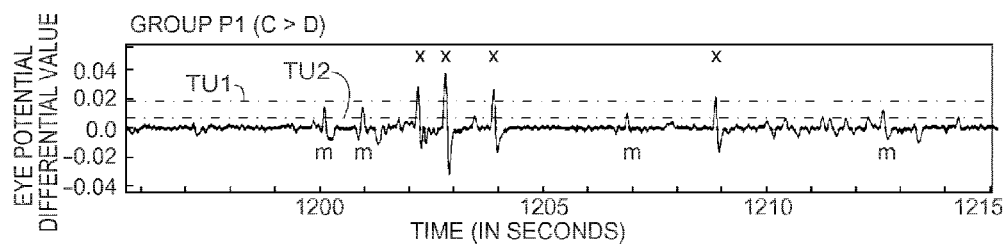
FIG. 5B is a diagram showing an example of time-series data on the eye potential differential values of a subject whose eyeblink occurrence interval is long, where X in the figures indicates a part in the video image where eyeblink occurrence is confirmed.

FIG. 5A shows an example of time-series data on the eye potential differential values obtained for a subject who is classified into P2 (group of short eyeblink occurrence interval), and FIG. 5B for a subject who is classified into P1 (group of long eyeblink occurrence interval), respectively, based on the frequency characteristic value according to the processing described above. During this measurement, the eye potential is measured and, at the same time, the image is captured via a video camera so that eyeblink occurrence can be confirmed. In the figures, TU1 and TU2 each indicate the upper threshold calculated by using the threshold coefficients respectively for group P1 and for group P2. The symbol X indicates a part where an eyeblink is confirmed in the image captured by the video camera, and the symbol m indicates a part where a waveform, which is estimated caused by an eyeball movement, is confirmed. As understood from each of FIG. 5A and FIG. 5B, the upper threshold calculated using the threshold coefficient corresponding to the respective group (that is, TU2 in FIG. 5A and TU1 in FIG. 5B) is a value that is smaller than the amplitude of an eyeblink waveform and is larger than the amplitude of a waveform m (non-eyeblink waveform) where an eyeblink does not occur. On the other hand, in the time-series data of group P1 (FIG. 5B), the upper threshold TU2, calculated using the threshold coefficient of group P2, is smaller than the amplitude of a non-eyeblink waveform, indicating in this case that an erroneous detection of an eyeblink waveform will occur. Similarly, in the time-series data of group P2 (FIG. 5A), when the upper threshold TU1, calculated using the threshold coefficient of group P1, is used, some eyeblink waveforms do not reach the upper threshold, indicating in this case that the omission of eyeblink waveform detection will occur. Actually, in the time-series data on the eye potential differential values of group P1 (group of long eyeblink occurrence interval) in which four eyeblinks are detected in the video-camera-captured image in the measurement example above, the four eyeblinks are detected correctly when the threshold calculated using the threshold coefficient of group P1 is used (correctness rate is 100%) (see TU1 in FIG. 5B). On the other hand, when the threshold calculated using the threshold coefficient of group P2 is used, the occurrence of 16 eyeblinks is detected with 12 eyeblinks detected erroneously (incorrect detection rate is 75%) (see TU2 in FIG. 5B). In addition, in the time-series data on the eye potential differential values of group P2 (group of short eyeblink occurrence interval) in which 15 eyeblinks are detected in the video-camera-captured image, the 15 eyeblinks are detected correctly when the threshold calculated using the threshold coefficient of group P2 is used (correctness rate is 100%) (see TU2 in FIG. 5A). On the other hand, when the threshold calculated using the threshold coefficient of group P1 is used, the occurrence of only four eyeblinks is detected with the detection of nine eyeblinks omitted (detection omission rate is 60%) (see TU1 in FIG. 5A). These results indicate that using the thresholds that are set according to the processing of the present disclosure described above reduces the erroneous detection, and the detection omission, of eyeblinks.

Thus, when eyeblink waveforms are detected using thresholds in the time-series data on the eye potential differential values, the configuration of the present disclosure allows the thresholds to be set appropriately based on the frequency characteristic of each subject, in particular, based on the ratio of the power of non-eyeblink waveform components to the power of an eyeblink waveform component. Therefore, this configuration reduces the detection omission of eyeblink waveform components and the erroneous detection in which a non-eyeblink waveform component is detected erroneously as an eyeblink waveform component.

Although embodiments of the present disclosure have been described above, it is to be understood that various modifications and changes may be easily added by those skilled in the art. It is apparent that the present disclosure is not limited to the embodiments described above but may be applied to various devices without departing from the concept of the present disclosure.

What is claimed is:

1. An eyeblink detection device comprising:
   circuitry configured to:
   generate time-series data on differential values of an eye potential of a subject;
   determine a frequency characteristic value from the time-series data on the eye potential differential values, the frequency characteristic value representing a frequency characteristic of the eye potential differential values;
   set a threshold coefficient based on the frequency characteristic value of the eye potential differential values;
   set an upper threshold and a lower threshold based on a number obtained by multiplying a standard deviation of the differential values in the time-series data on the eye potential differential values by the threshold coefficient, the upper threshold and the lower threshold being used for detecting an eyeblink waveform in the time-series data on the eye potential differential values;
   detect a change in the eye potential differential values as the eyeblink waveform, the change occurring in the time-series data either when the eye potential differential value becomes larger than the upper threshold and, after that, changes from the upper threshold to the lower threshold within a predetermined time or when the eye potential differential value becomes smaller than the lower threshold and, after that, changes from the lower threshold to the upper threshold within the predetermined time; and
   output an eyeblink detection result based on the eyeblink waveform to a display.

2. The eyeblink detection device according to claim 1, wherein
   the frequency characteristic value is a value representing a ratio of a power of non-eyeblink waveform components to a power of an eyeblink waveform component in the time-series data on the eye potential differential values, and the circuitry is configured to set the threshold coefficient larger when the frequency characteristic value is large than when the frequency characteristic value is small.

3. The eyeblink detection device according to claim 1, wherein the circuitry is configured to calculate a frequency spectrum of the time-series data on the eye potential differential values, and the frequency characteristic value is a value representing a ratio of a power of non-eyeblink waveform components to a power of an eyeblink waveform component in the frequency spectrum of the eye potential differential values.

4. The eyeblink detection device according to claim 1, wherein the frequency characteristic value is a ratio of a maximum value of a power of non-eyeblink waveform components to a power of an eyeblink waveform component and the threshold coefficient when the frequency characteristic value is large is set larger than when the frequency characteristic value is small.

5. The eyeblink detection device according to claim 1, wherein the frequency characteristic value is a sum of powers of a frequency spectrum and the threshold coefficient when the frequency characteristic value is large is set larger than when the frequency characteristic value is small.

6. The eyeblink detection device according to claim 1, wherein the subject is classified into one of groups based on the frequency characteristic value and the threshold coefficient is set for each of the groups into which the subject is classified.

7. The eyeblink detection device according to claim 1, wherein an interval width of the time series data used for calculating the standard deviation of the differential values in the time-series data on the eye potential differential values is set based on the frequency characteristic value.

8. The eyeblink detection device according to claim 1, wherein the circuitry is configured to detect an eyeblink time in the detected eyeblink waveform.

9. The eyeblink detection device according to claim 1, wherein the circuitry includes a signal processing device.

10. The eyeblink detection device according to claim 9, wherein the signal processing device includes a central processing unit and a storage device.

11. The eyeblink detection device according to claim 1, further comprising a sensor configured to measure the eye potential of the subject.

12. The eyeblink detection device according to claim 11, wherein the sensor includes an electrode configured to measure the eye potential of the subject.

13. The eyeblink detection device according to claim 11, wherein the sensor includes a plurality of electrodes configured to measure the eye potential of the subject.

14. The eyeblink detection device according to claim 1, further comprising the display.

* * * * *